(12) United States Patent
Aders et al.

(10) Patent No.: US 11,963,871 B2
(45) Date of Patent: Apr. 23, 2024

(54) CRIMPING DEVICES AND METHODS

(71) Applicant: Edwards Lifesciences Corporation, Irvine, CA (US)

(72) Inventors: Nicholas Brandon Aders, Santa Ana, CA (US); Kristen Hicks, Irvine, CA (US); Gil Senesh, Laguna Beach, CA (US); Michael R. Bialas, Lake Forest, CA (US); Tung T. Le, Costa Mesa, CA (US); Sean Chow, Irvine, CA (US); Thanh Huy Le, Oceanside, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/080,043

(22) Filed: Dec. 13, 2022

(65) Prior Publication Data
US 2023/0103353 A1  Apr. 6, 2023

Related U.S. Application Data

(63) Continuation of application No. PCT/US2021/037738, filed on Jun. 17, 2021.
(Continued)

(51) Int. Cl.
| | |
|---|---|
| *B23P 11/00* | (2006.01) |
| *A61F 2/24* | (2006.01) |
| *A61F 2/95* | (2013.01) |

(52) U.S. Cl.
CPC ........... *A61F 2/2433* (2013.01); *B23P 11/005* (2013.01); *A61F 2/9524* (2020.05); *A61F 2240/001* (2013.01); *A61F 2250/0039* (2013.01)

(58) Field of Classification Search
CPC .................. B23P 11/005; A61F 2/2412; A61F 2240/001; A61F 2250/0039; A61F 2/9522;
(Continued)

(56) References Cited

U.S. PATENT DOCUMENTS

| | | | |
|---|---|---|---|
| 3,409,013 A | 11/1968 | Berry | |
| 3,548,417 A | 12/1970 | Kisher | |

(Continued)

FOREIGN PATENT DOCUMENTS

| | | |
|---|---|---|
| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Cathether Technique in Closed Chest Pig," European Heart Journal, No. 13. pp. 704-708. 1992.
(Continued)

*Primary Examiner* — Matthew P Travers
(74) *Attorney, Agent, or Firm* — Klarquist Sparkman, LLP; Joel B. German

(57) ABSTRACT

Devices and methods for crimping a prosthetic heart valve onto a delivery device are described. In some embodiments, valves are crimped over an inflatable balloon and between proximal and distal shoulders mounted on a shaft inside the balloon. Crimping methods can include multiple compression steps with the valve located in different axial positions relative to the crimping jaws at each different step. In some methods, the valve may extend partially outside of the crimping jaws during certain crimping steps, such that the crimping force is only applied to the part of the valve that is inside the jaws. Exemplary crimping devices can include two or more adjacent sets of jaws that close down to
(Continued)

different inner diameters, such that different parts of a valve get compressed to different outer diameters at the same time during a single crimping step.

17 Claims, 6 Drawing Sheets

Related U.S. Application Data

(60) Provisional application No. 63/041,050, filed on Jun. 18, 2020.

(58) Field of Classification Search
CPC ...... A61F 2/9524; A61F 2/243; A61F 2/2433; Y10T 29/49908–49909; Y10T 29/49913
See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |

(56) References Cited

U.S. PATENT DOCUMENTS

| | | |
|---|---|---|
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Fidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,474,122 B2 * | 7/2013 | Melsheimer ............. B30B 9/00 29/508 |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 11,224,509 B2 | 1/2022 | Dasi et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |

(56) References Cited

U.S. PATENT DOCUMENTS

| | | | |
|---|---|---|---|
| 2015/0135506 A1 | 5/2015 | White | |
| 2015/0157455 A1 | 6/2015 | Hoang et al. | |
| 2016/0374802 A1 | 12/2016 | Levi et al. | |
| 2017/0014229 A1 | 1/2017 | Nguyen-Thien-Nhon et al. | |
| 2018/0028310 A1 | 2/2018 | Gurovich et al. | |
| 2018/0153689 A1 | 6/2018 | Maimon et al. | |
| 2018/0185183 A1* | 7/2018 | Christakis | A61F 2/966 |
| 2018/0325665 A1 | 11/2018 | Gurovich et al. | |
| 2018/0344456 A1 | 12/2018 | Barash et al. | |
| 2019/0159894 A1 | 5/2019 | Levi et al. | |
| 2019/0192288 A1 | 6/2019 | Levi et al. | |
| 2019/0192289 A1 | 6/2019 | Levi et al. | |
| 2022/0008235 A1* | 1/2022 | Risch | A61F 2/9522 |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| NO | 9933414 A1 | 7/1999 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0047139 A9 | 9/2001 |
| WO | 0164137 A1 | 9/2001 |
| WO | 0176510 A2 | 10/2001 |
| WO | 0222054 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 | 6/2003 |
| WO | 2005034812 A1 | 4/2005 |
| WO | 2005055883 A1 | 6/2005 |
| WO | 2005084595 A1 | 9/2005 |
| WO | 2005102015 A2 | 11/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2009053497 A1 | 4/2009 |
| WO | 2009061389 A2 | 5/2009 |
| WO | 2009094188 A2 | 7/2009 |
| WO | 2009116041 A2 | 9/2009 |
| WO | 2009149462 A2 | 12/2009 |
| WO | 2010011699 A2 | 1/2010 |
| WO | 2010121076 A2 | 10/2010 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

* cited by examiner

CRIMPING DEVICES AND METHODS

CROSS-REFERENCE TO RELATED APPLICATIONS

This application is a continuation of PCT Application No. PCT/US2021/037738, filed Jun. 17, 2021, which application claims the benefit of U.S. Provisional Patent Application No. 63/041,050, filed Jun. 18, 2020, which is incorporated by reference herein in its entirety.

FIELD

This application is related to crimping devices and methods for prosthetic heart valves, stents, and the like.

BACKGROUND

Crimping a prosthetic heart valve onto a catheter-based delivery system is typically done using crimping devices that have a set of jaws that form a single continuous face as they close, which compresses the valve equally along its length to a smaller diameter. Typically, the entire valve is positioned within the jaws as jaws close, which applies crimping forces uniformly across the axial length of the valve and uniformly reduces the whole valve at the same rate to the same final crimped diameter.

SUMMARY

Disclosed herein are novel devices and methods for crimping a prosthetic heart valve onto a delivery device. In some embodiments, valves are crimped over an inflatable balloon and between proximal and distal shoulders mounted on a shaft inside the balloon. Crimping methods disclosed herein can include multiple compression steps with the valve located in different axial positions relative to the crimping jaws at each different step. In some methods, the valve may extend partially outside of the crimping jaws during certain crimping steps, such that the crimping force is only applied to the part of the valve that is inside the jaws. Exemplary crimping devices disclosed herein can include two or more sets of side-by-side jaws that close down to different inner diameters, such that different parts of a valve get compressed to different outer diameters at the same time during a single crimping step.

Exemplary methods can comprise any combination of the following steps: inserting a prosthetic heart valve into a crimping device in a radially expanded state such that the valve is positioned within crimping jaws of the crimping device; positioning an inflatable balloon of the delivery device within the valve; positioning the valve and the delivery device in a first axial position where the valve and at least part of the distal shoulder of the delivery device are within the jaws between the proximal and distal ends of the jaws, and where the entire proximal shoulder is outside of the jaws proximal to the proximal end of the jaws; closing and opening the jaws with the valve and delivery device in the first axial position, such that the valve is at least partially crimped onto the balloon between the proximal shoulder and the distal shoulder; repositioning the valve and delivery device from the first axial position to a second axial position where a first distal portion of the valve and at least part of the distal shoulder are within the jaws, and where a first proximal portion of the valve and the proximal shoulder are outside of the jaws proximal to the proximal end of the jaws; closing and opening the jaws with the valve and delivery device in the second axial position; repositioning the valve and delivery device from the second axial position to a third axial position where a second distal portion of the valve and at least part of the distal shoulder are within the jaws, and where a second proximal portion of the valve and the proximal shoulder are outside of the jaws proximal to the proximal end of the jaws, wherein the second distal portion is axially shorter than the first distal portion, and the second proximal portion is axially longer than the first proximal portion; closing and opening the jaws with the valve and delivery device in the third axial position; repositioning the valve and delivery device from the third axial position to a fourth axial position where the entire valve and at least part of the proximal shoulder are within the jaws, and where the entire distal shoulder is outside of the jaws distal to the distal end of the jaws; and closing and opening the jaws with the valve and delivery device in the fourth position.

Exemplary crimping devices can comprise: first jaws having an open position and a fully closed position, wherein the first jaws have a first inner diameter in the fully closed position, and second jaws having an open position and a fully closed position, wherein the second jaws have a second inner diameter in the fully closed position, and wherein the second inner diameter is smaller than the first inner diameter. The first jaws and the second jaws can be axially side-by-side, and/or in contact with each other. The first jaws can have a greater axial dimension than the second jaws, such as at least two time or at least five times greater. The first inner diameter and the second inner diameter can be selected to correspond to desired outer diameters of prosthetic heart valve that is crimped by the device. The first jaws and the second jaws can be actuated at the same time using a common actuator, such as a handle that the user pulls.

The foregoing and other objects, features, and advantages of the disclosed technology will become more apparent from the following detailed description, which proceeds with reference to the accompanying figures.

DETAILED DESCRIPTION

General Considerations

Figure 1A:
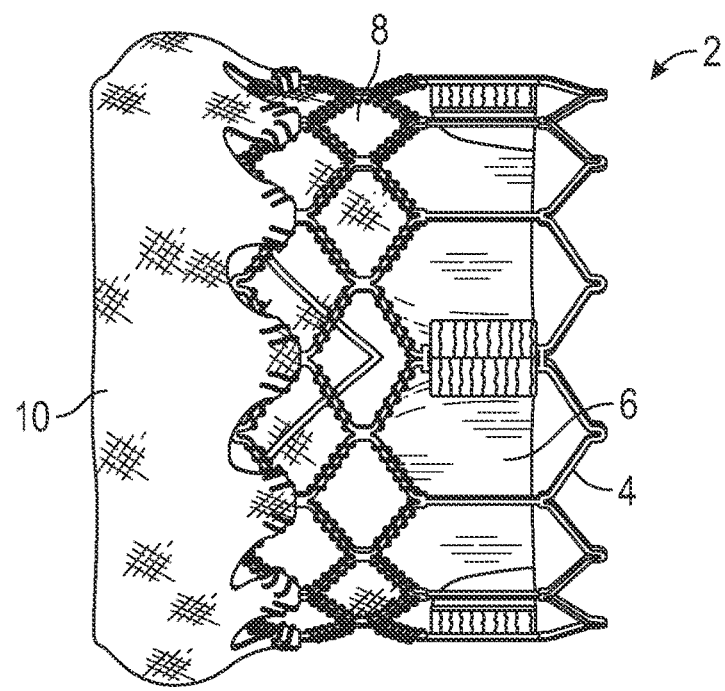
FIG. 1A shows an exemplary prosthetic heart valve in a radially expanded state.

It should be understood that the prosthetic heart valves described herein can be adapted for delivering and implanting in any of the native annuluses of the heart (e.g., the aortic, pulmonary, mitral, and tricuspid annuluses), and can be used with any of various delivery devices for delivering the prosthetic valve using any of various delivery approaches (e.g., retrograde, antegrade, transseptal, transventricular, transatrial, etc.). Crimping devices disclosed herein can be used with any suitable types of prosthetic heart valves, including those described herein, and can be used in conjunction with any of various delivery devices for delivering the prosthetic valve using any of various delivery approaches.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." As used herein, "and/or" means "and" or "or", as well as "and" and "or". Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same.

The valves and frames disclosed herein are described using an axial direction defined by the centerline of the annular frame and the overall blood flow direction from an inflow end to an outflow end, a radial direction that is defined as radiating perpendicularly from the centerline of the frame, and a circumferential direction that is perpendicular to the axial and radial directions and extends around the centerline of the frame. The crimping device and crimping jaws disclosed herein are described using axial and radial directions that are defined by the axial and radial dimensions of a valve that is crimped by the device. The term "inner" refers to objects, surfaces, and areas proximal to the centerline of the frame or device and the term "outer" refers objects, surfaces and areas that are farther from the centerline of the frame or device.

In view of the many possible embodiments to which the principles of the disclosed technology may be applied, it should be recognized that the illustrated embodiments are only preferred examples of the technology and should not be taken as limiting the scope of the technology. Rather, the scope of the disclosed technology is at least as broad as the appended claims.

Examples of the Disclosed Technology

It is sometimes desirable to compress certain regions of a valve, stent, or similar device to a smaller diameter, such as to protect apexes from snagging or to create a football-like shape and aid insertion into a catheter. Some crimping devices disclosed herein include stacked side-by-side jaw sets which are able to move independently or together as one to crimp a device to different diameters along its length. The use of stacked jaw sets which are capable of independent motion has several advantages to current designs. Some embodiments can allow for a continuous unified jaw face through a portion of the crimping process, which can be critical to prevent frame damage due to snags during axial expansion, while allowing a section of the jaws to compress a region to a smaller diameter at the end of the process. This allows a user to do things like tuck in apexes to prevent snagging, or create a football-like shapes to aid insertion or device loading. Some crimping devices can achieve this motion without requiring any additional action from the operator beyond the basic actions used in a normal crimper. As the handle is rotated, the crimper jaws can start their motion together and end at different stopping positions. These features can improve device performance without requiring complex multi-stage crimping procedures.

In addition to novel crimping devices, novel methods described herein that can also be used to crimp a device in a more desirable manner using a conventional crimper having only one set of jaws. In a conventional crimping method, an expanded device is placed inside the crimping aperture and the uniform jaws compress the device uniformly to a compressed state, such that all parts of the device are radially compressed at the same rate and to the same diameter, and then the jaws are released. The resulting shape of the crimped device may not be uniform, as some parts of the device may deform more than other or recoil more than others. Thus, the final shape of the crimped device is inherent based on the structure of the device (e.g., the amount of material inside a valve frame, thicknesses of the frame, outer skirts, etc.). However, this conventional approach can result in the crimped device having undesirable shape properties, which can lead to harmful outcomes for a patient. For example, parts of the device that project too far outwards can catch on the sheath, vessels, or native valve region and can prevent the device from successfully travelling to the implant location.

Some methods disclosed here include purposeful shaping of device through multi-stage crimping processes, which can allow a person to target a more desirable crimped profile for the device for passing through the anatomy to the implant location. This changes the crimped device shape from being dependent solely on the device design and shifts it to being controlled also by an optimized preparation procedure. This can decrease the likelihood of an adverse event due to the valve catching on the sheath, vessels, or annulus, for example.

A desirable crimped profile is one in which the leading edge of the device is most protected. Such protection can result from a combination of how large the diameter is of the distal end of the delivery system compared to how small the diameter is of the distal edge of the device crimped onto the delivery system. Targeted crimping in certain portions of the device can help achieve such a desirable crimped profile. For example, using a prosthetic heart valve as an exemplary device to be crimped, targeted crimping can be performed by placing only certain axial sections of the valve within the crimping jaws such that one axial portion receiving compressing force while portions that are distal to the jaws and/or proximal to the jaws receive no direct crimping force from the jaws. This can concentrate the crimping forces over only one axial portion of the valve, rather than being spread evenly across the whole axial length of the valve. This can result in smaller crimped diameters in the targeted portions of the valve, such the distal or leading edge of the valve. Crimping the leading edge to a smaller diameter can help the leading edge be more protected by distal portions of the delivery device, which can help the crimped valve better pass through a sheath, vessels, etc., without catching.

FIG. 1A shows an exemplary prosthetic heart valve 2 that can be used with the herein disclosed crimping devices and crimping methods. The valve 2 is just one example, and many other implantable device can be used as well, including stents, valves, frames, and any other radially compressible device. Such device can include annular frames, such as the frame 4, that are radially compressible to be mounted on a delivery device and later radially expandable within a patient's body. Such frames can include self-expandable frames (e.g., made of superelastic materials) and balloon-expandable frames (e.g., made of cobalt chromium or stainless steel). The crimped device can also include various other components, such as a leaflet structure 6, an inner skirt 8, and/or an outer skirt 10. The valve 2 can be configured for placement at a native aortic valve region of heart, while other subject devices can be configured for placement at other heart locations or other parts of the body. In the example of FIG. 1A, the outer skirt 10 is positioned at a blood inflow end of the valve 2, with the opposite end being a blood outflow end of the valve.

Figure 1B:
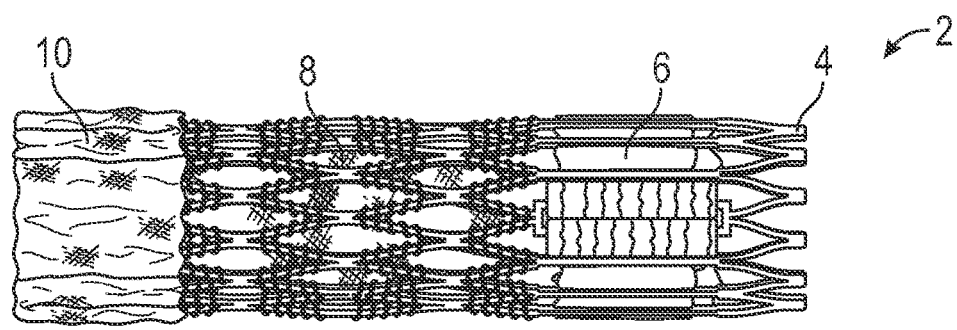
FIG. 1B shows the valve of FIG. 1A in a radially compressed state.

FIG. 1A shows the valve 2 in a radially expanded state, while FIG. 1B shows the valve in a radially compressed or crimped state. In the crimped state, the valve 2 has a smaller radial dimension (i.e., its outer diameter) and a longer axial dimension (i.e., its axial length). Some parts of the valve 2 can have slightly different outer diameters when in the crimped state. For example, in some circumstances the axial zone including the outer skirt 10 can be slightly bulkier and have a larger outer diameter compared to other portions of the valve. However, with the herein disclosed technologies, the final crimped state of a device can be better customized and controlled, such that the outer diameters at different axial locations along the valve are not just a result of the structure of the device itself, but also a result of the crimping method used and/or the type of crimping device used.

Figure 2:
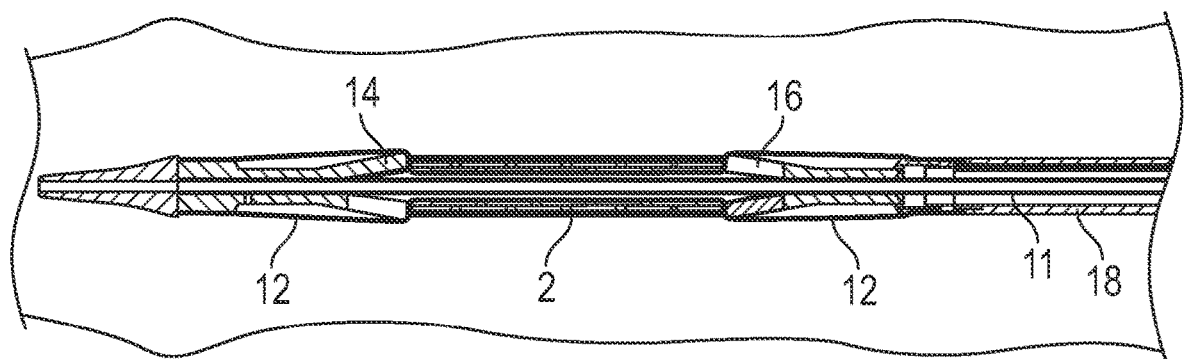
FIG. 2 is a cross-sectional view of a distal end of an exemplary delivery device that includes a valve in a radially compressed state mounted over an inflatable balloon.

FIG. 2 shows a distal end portion of an exemplary delivery device with the valve 2 crimped onto it. Other delivery devices can also be used with the herein disclosed technology. In the example of FIG. 2, the valve is crimped onto a shaft 11 over an inflatable balloon 12 between a distal shoulder 14 and a proximal shoulder 16. The shoulders 14 and 16 can be positioned around the shaft 11 within the balloon 12. When the valve 2 is crimped onto the delivery device, the shoulders 14, 16 can provide protection to the ends of the valve 2 to help prevent the ends of the valve from snagging on a catheter wall, a vessel wall, or other structure while the valve is being delivered. The shoulders can also help keep the valve from migrating axially relative to the inner shaft 11. However, crimping the ends of the valve (particularly the distal end of the valve adjacent the distal stop 14) to a small outer diameter than the rest of the valve can also help keep the valve from snagging or migrating. When the valve 2 is delivered to the implantation location, the balloon 12 can be inflated to radially expand the valve and implant it in the aortic valve region (or other target location).

Figure 3:
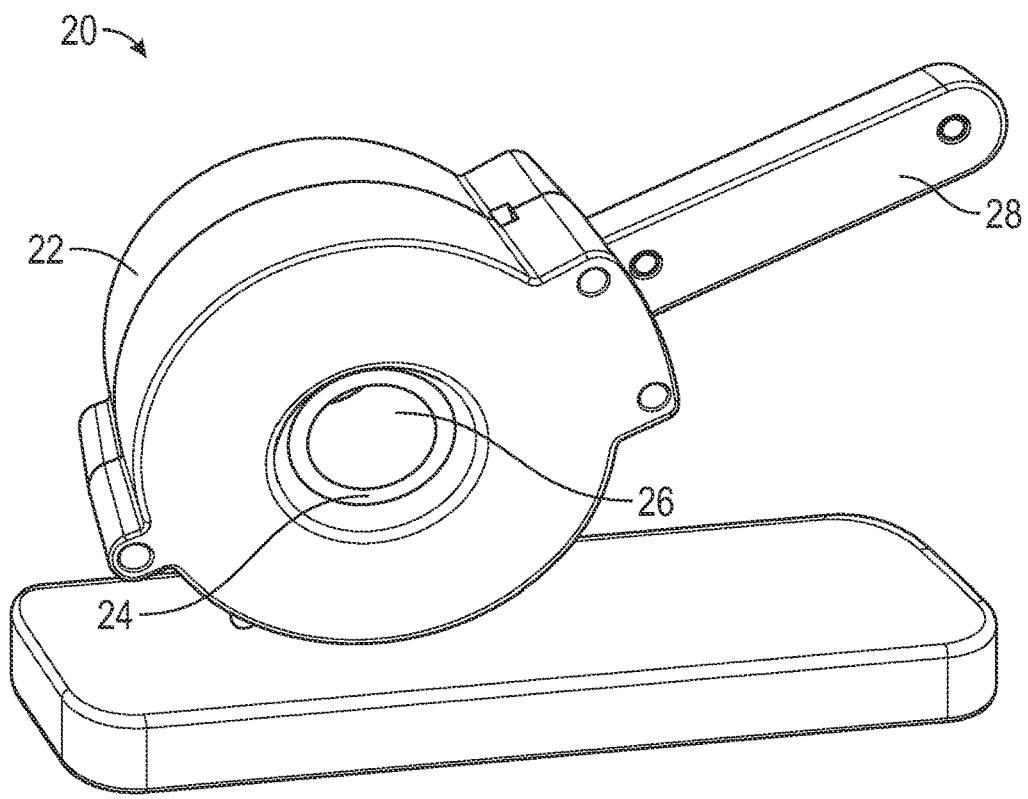
FIG. 3 shows an exemplary crimping device in an open position.
Figure 4:
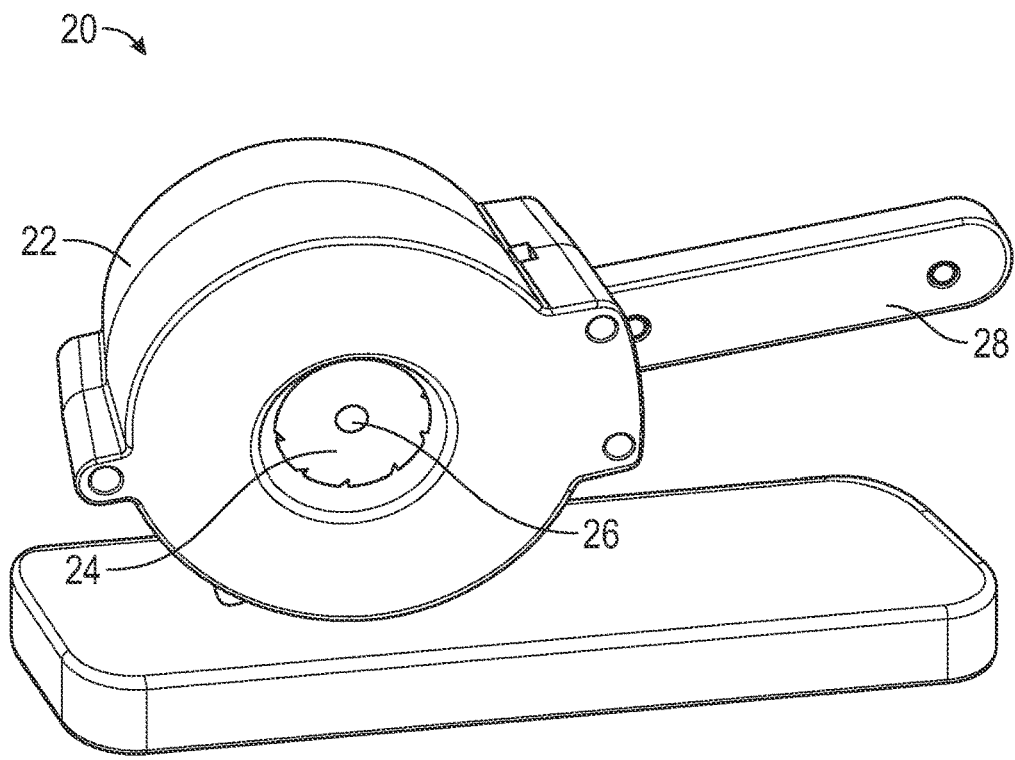
FIG. 4 shows the crimping device of FIG. 3 in a closed position.

FIGS. 3 and 4 illustrate an exemplary crimping device, or crimper, 20 that is used to crimp a prosthetic heart valve onto a delivery device. The crimper 20 comprises an outer housing 22 and crimping jaws 24 with a central opening 26 and an actuation handle 28. A radially expanded valve is placed in the opening 26 with the jaws 24 open (FIG. 3). With a delivery device positioned within the expanded valve, the handle 28 is actuated to cause the jaws 24 to closed down (FIG. 4) and crimp the valve onto the delivery device. The jaws 24 comprise several individual pieces that all move inwardly in unison to uniformly reduce the diameter of the opening 26 and apply even crimping pressure around the valve. When the handle 28 is released, the jaws open up and the delivery device with the valve mounted thereon can be removed or repositioned for another round of crimping.

FIGS. 5-9 illustrate exemplary crimping steps. Various novel multi-stage crimping methods can include any combination of the steps illustrated in FIGS. 5-9 and/or other acts. For example, the steps in FIGS. 5-9 can all be performed sequentially. In some methods, the step of FIG. 7 may not be included, or the step of FIG. 8 may not be included, or the step of FIG. 9 may not be included. In other examples, additional crimping steps are performed in addition to, or in place of, the steps shown in FIGS. 5-9.

In FIGS. 5-9, the crimping jaws 40 are illustrated with simple rectangles that represent a typically annular array of crimping jaws, like those shown in FIGS. 3 and 4. The jaws 40 include a first axial end 70 and an opposing second axial end 72. A valve can be inserted into the jaws 40 from either axial end. While the jaws 40 comprise multiple individual jaw pieces that abut each other to form an annular structure, collectively the radially inner surfaces of the jaws 40 can be generalized as forming a smooth, uniform diameter, cylindrical inner surface extending between the axial ends 70 and 72.

Figure 5:
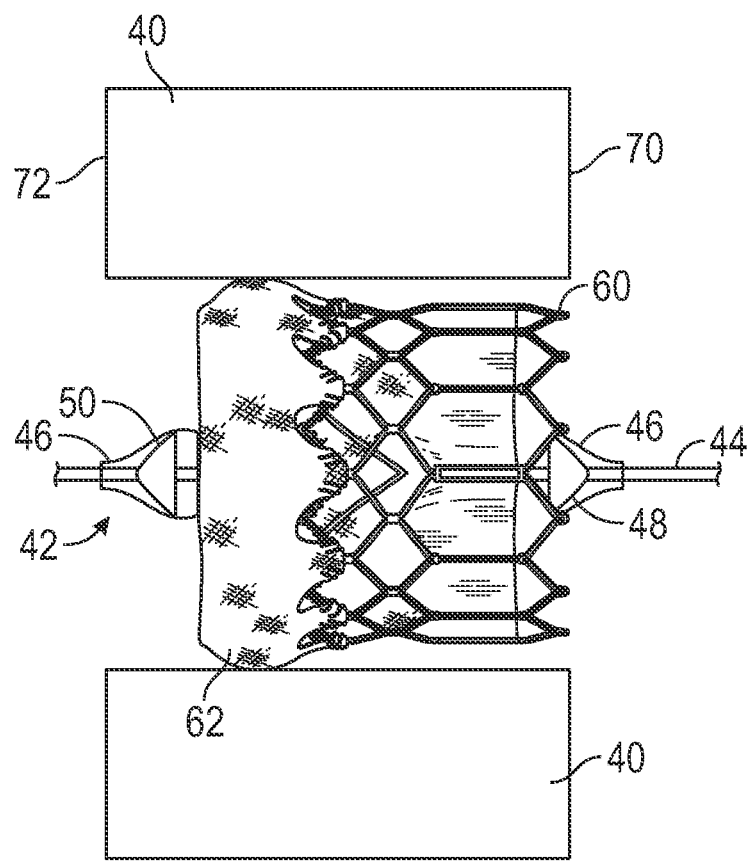
FIG. 5 is a cross-sectional view of a crimping device in an open position with a radially expanded valve and the delivery device inside the crimping jaws in a first axial position.

In FIG. 5 the jaws 40 are open, similar to FIG. 3, while in FIGS. 6-9 the jaws are closed, similar to FIG. 4. In FIG. 5, a radially expanded valve 42 is positioned within the jaws 40 with a delivery device positioned within the valve. The valve is positioned such that a proximal end of the valve (right side) is about even with the first axial end 70 of the jaws, and the delivery device is positioned to match the position of the valve. The delivery device in this example includes an inner shaft 44, an inflatable balloon 46, a proximal shoulder 48, and a distal shoulder 50. The valve is oriented axially between the two shoulders. The distal shoulder 50 is at least partially positioned within the jaws 40, while the proximal shoulder 48 is positioned outside of the jaws, proximal to the first axial end 70 of the jaws.

Figure 6:
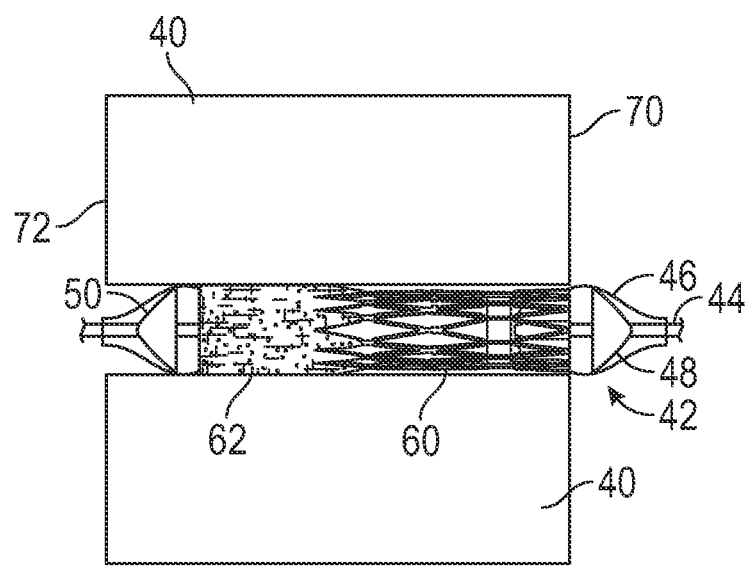
FIG. 6 shows crimping jaws of FIG. 5 in a closed position having radially compressed the valve onto the delivery device in the first axial position.

FIG. 6 shows the configuration after the jaws 40 are closed down from the position of FIG. 5, radially compressing the valve around the inner shaft 44 and balloon 46, between the shoulders 48 and 50. In this crimping step, the whole valve is within the jaws and receives uniform crimping contact across the valve from the jaws. After reopening the jaws from the configuration of FIG. 6, the valve remains radially compressed due to the plastic deformation of the valve frame 60 (e.g., a cobalt chromium alloy frame).

Figure 7:
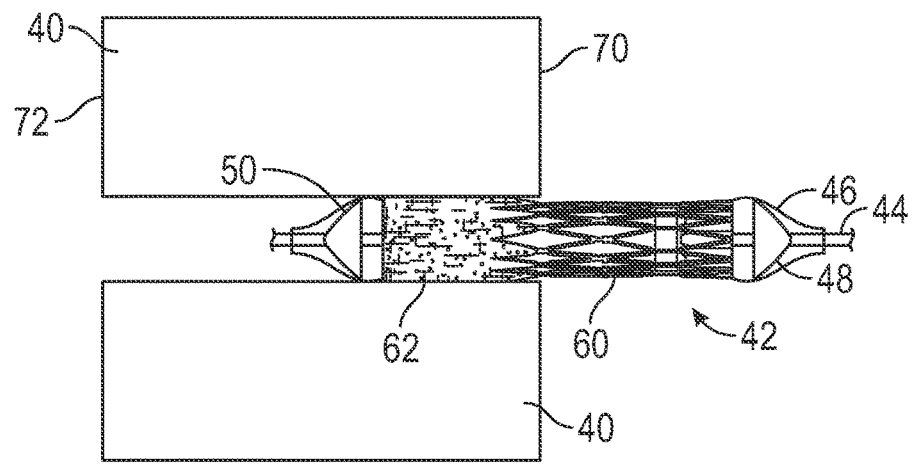
FIG. 7 shows the valve of FIG. 5 in a second axial position where a distal portion of the valve is in the jaws and a proximal portion of the valve is outside the jaws.

In FIG. 7, the delivery device and valve have been shifted axially after the crimping step of FIG. 6. In the configuration of FIG. 7, a distal portion of the valve is still within the jaws while a proximal portion of the valve is outside the first axial end 70 of the jaws. The valve may be about half in and half out of the jaws in this position, for example. As shown in FIG. 7, the blood inflow end of the valve that includes the outer skirt 62 is within the jaws. This is also the distal end of the valve as mounted on the delivery device. In FIG. 7, the distal portion of the valve receives a second crimping from the jaws while the proximal portion of the valve does not. This can result in the distal portion of the valve having a smaller outer diameter than the proximal portion of the valve (though this difference in outer diameters is not shown in the figures).

Figure 8:
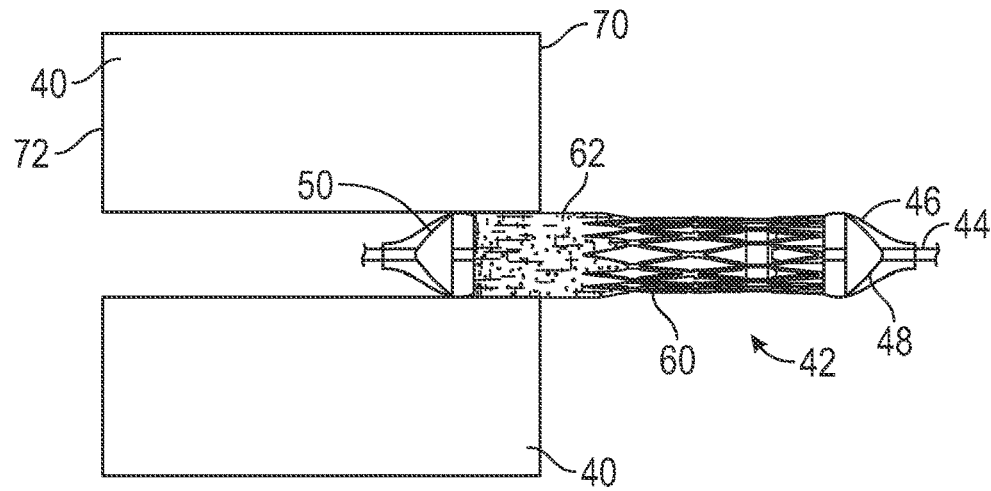
FIG. 8 shows the valve of FIG. 5 in a third axial position where a shorter distal portion of the valve is in the jaws and a longer proximal portion of the valve is outside the jaws.

In FIG. 8, the delivery device and valve have been shifted further axially after the crimping step of FIG. 7. In the configuration of FIG. 8, a distal portion of the valve is still within the jaws, though the axial length of the distal portion within the jaws is shorter than in the position of FIG. 7. Similarly, the axial length of the proximal portion of the valve that is outside the first axial end 70 of the jaws is longer than in the position of FIG. 7. The valve may be about one forth in and three fourths out of the jaws in this position, for example. As shown in FIG. 8, about half of the outer skirt 62 is within the jaws, and only that portion of the valve receives a crimping from the jaws. This can result in the distal end of the valve having an even smaller outer diameter.

In the crimping steps of FIGS. 6, 7, and 8, the distal shoulder may also be radially compressed by the jaws, depending on the size and configuration of the shoulders and how far the jaws close radially. In some embodiment, the shoulders can have slots or other features that allow them to radially compress. The shoulders can be comprised of elastic material that resiliently deforms under compression and then returns to its original shape when compression is released. This can allow the jaws to compress the distal end of the valve to a smaller outer diameter than the outer diameter of the distal shoulder, as the shoulder can re-expand to a slightly larger diameter than the distal end of the valve after the compression from the jaws is released. This can allow the distal end of the valve to be "tucked in" behind the distal shoulder so that the shoulder shields the distal end of the valve from snagging or catching during delivery. The same can be true for the proximal end of the valve and the proximal shoulder 48 in some embodiments.

Figure 9:
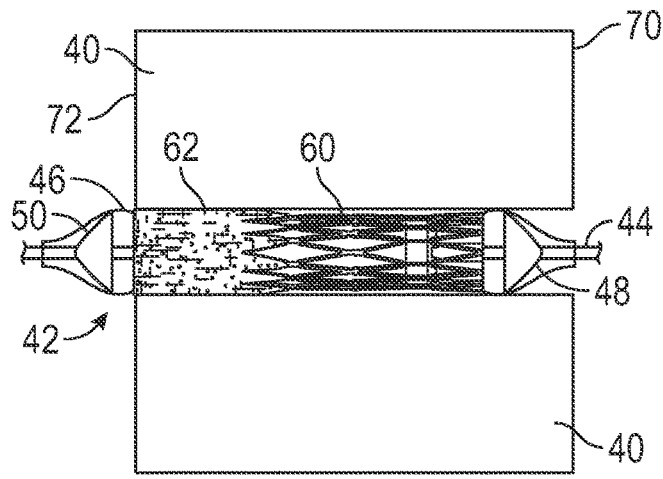
FIG. 9 shows the valve of FIG. 5 in a fourth axial position where the entire valve is in the jaws and a distal shoulder of the delivery device is outside the jaws.
Figure 10:
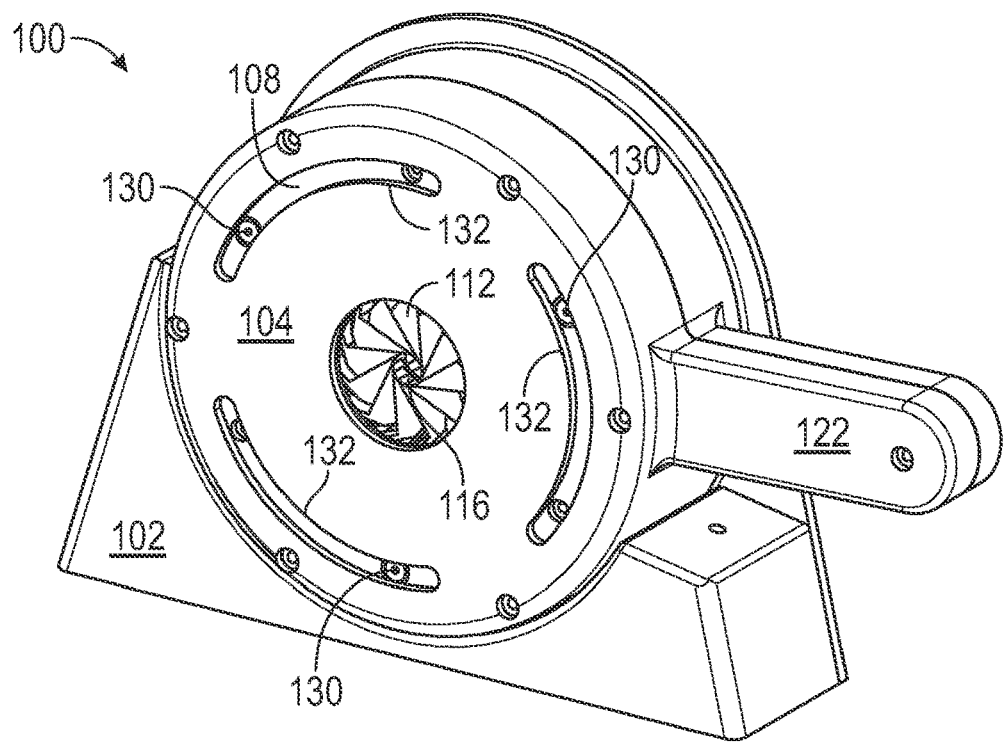
FIG. 10 shows an exemplary crimping device that has two sets of crimping jaws that closed to two different diameters.
Figure 11:
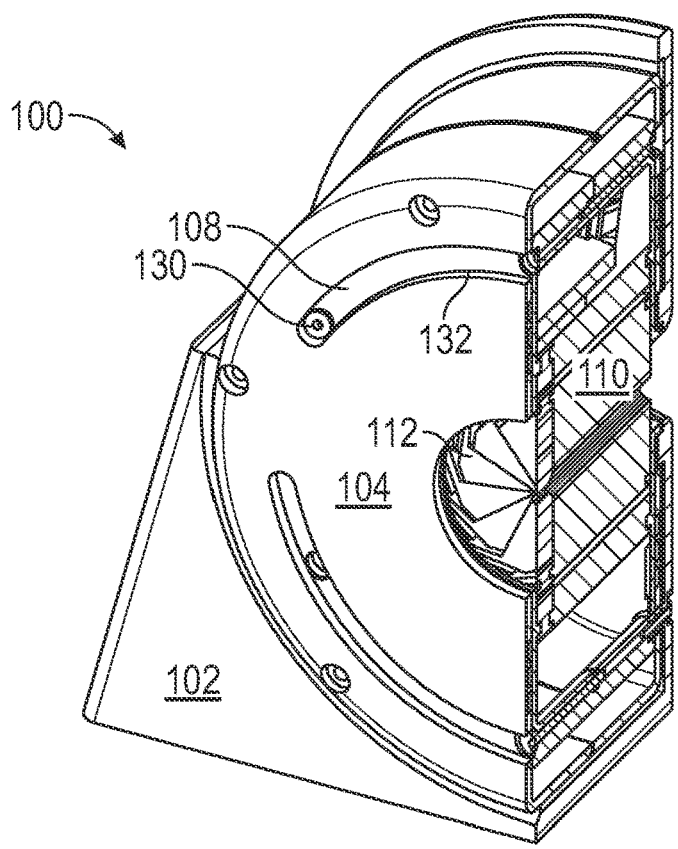
FIG. 11 is a cross-sectional view of the device of FIG. 10 in a closed position.
Figure 13:
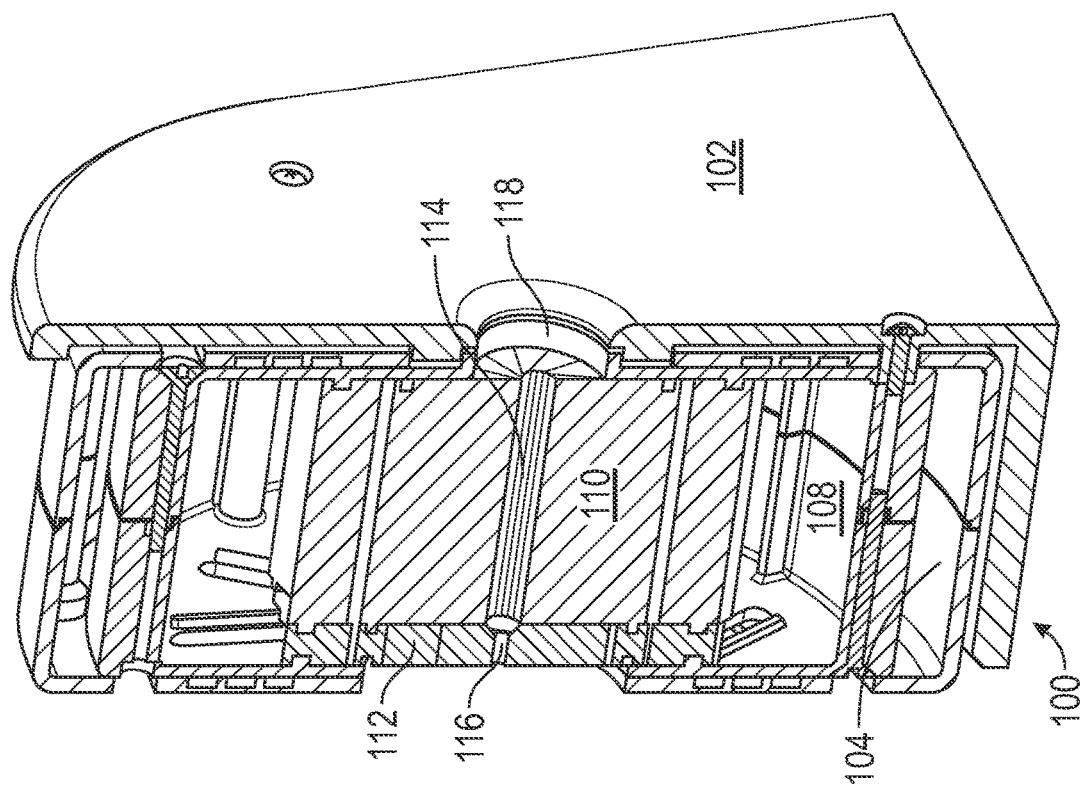
FIG. 13 is yet another cross-sectional view of the device of FIG. 10.

FIG. 9 illustrates another crimping step where at least part of the proximal shoulder 48 is within the jaws and receives compression along with the proximal end of the valve. In the position of FIG. 9, the entire valve is within the jaws with the distal end of the valve is aligned with the second axial end 72 of the jaws. At least part of the proximal shoulder 48 is also within the jaws, while the distal shoulder 50 is outside the jaws. When the crimping step of FIG. 9 occurs after the previous crimping steps of FIGS. 6-8 (or at least after the step of FIG. 6), the whole valve may already be radially compressed, and so this step can be more of a finishing step to recompress the valve in case any part of the valve is sticking out or bulging, etc. For example, the parting crimping steps of FIGS. 7 and 8 can possible cause the free proximal end of the valve to expand a little, and the full crimping step of FIG. 9 can recompress the proximal end to ensure the valve is fully crimped as desired. In addition, compressing the proximal end of the balloon 46 while the distal end of the balloon is outside the jaws, as in FIG. 9, can beneficially cause fluid within the balloon to travel distally into the free distal end of the balloon and partially inflate the distal end of the balloon. Partially inflating the distal end of the balloon can cause the balloon to bulge out slightly beyond the diameter of the distal end of the valve and thereby help protect the distal end of the valve from snagging or catching during delivery.

Figure 12:
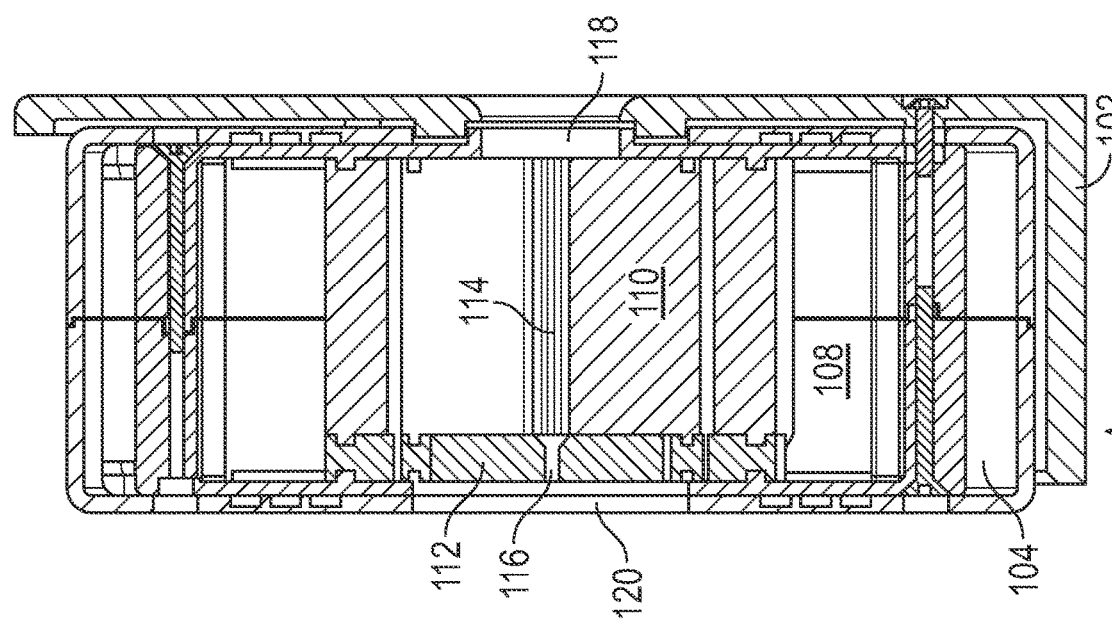
FIG. 12 is another cross-section view of the device of FIG. 10.

FIGS. 10-13 illustrate an exemplary crimping device 100 that include two sets of jaws that close to two different minimum diameters. The device 100 can be used to crimp a valve onto a delivery device while compressing one section of the valve to a larger outer diameter and compressing a second section of the valve to a smaller outer diameter, using a single crimping action. The device 100 can comprise a support base 102, an outer housing 104 with a handle 122, an inner frame 108, a first set of jaws 110, and a second set of jaws 112. The base, outer housing, and inner frame can form a central opening 118 that passes through the device and is configured to receive a valve and delivery device. The two sets of jaws 110, 112 are positioned side-by-side as shown in FIG. 12 and align with the central opening 118.

The outer housing 104 includes slots 132 in a lateral face and projections 130 of the inner frame 108 extend into the slots 132. Similarly, lateral aspects of the jaws 110, 112 engage with the inner frame 108 via a series of projections and slots. When the handle 122 is actuated, the outer housing rotates relative to the base 102, causing the two sets of jaws to close at the same time.

The jaws 110 and 112 have an open configuration where they form a wide opening that aligns with the central opening 118, and the jaws also each have a closed configuration where they form smaller contracted openings, with the first set of jaws 110 forming a first contracted opening 114 and the second set of jaws 112 forming a second contracted opening 116 that has a smaller diameter than the first contracted opening.

When a valve is crimped onto a delivery device using the device 100, the part of the valve that is within the second set of jaws 112 gets compressed down to a smaller diameter than the part of the valve that is within the first set of jaws 110. For example, the distal or leading end of the valve when mounted on the delivery device can be crimped to a smaller diameter by the second set of jaws while the proximal portion of the valve is crimped by the first set of jaws. The benefits of having the distal leading end of the valve be crimped to a smaller diameter are described elsewhere herein, such as in relation to the multi-stage crimping methods. A benefit of using a multi jaw crimping to accomplish this is that it can be done in a single crimping step, with one compression step, as compared to multiple steps using a conventional crimper.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A method of crimping a prosthetic heart valve onto a delivery device, comprising: inserting the valve into a crimping device in a radially expanded state such that the valve is positioned within crimping jaws of the crimping device, the crimping jaws having a proximal end and a distal end; positioning an inflatable balloon of the delivery device within the valve, the delivery device comprising a proximal shoulder and a distal shoulder positioned within the balloon; positioning the valve and the delivery device in a first axial position where the valve and at least part of the distal shoulder are within the jaws between the proximal and distal ends of the jaws, and where the entire proximal shoulder of the delivery device is outside of the jaws proximal to the proximal end of the jaws; closing and opening the jaws with the valve and delivery device in the first axial position, such that the valve is at least partially crimped onto the balloon between the proximal shoulder and the distal shoulder; repositioning the valve and delivery device from the first axial position to a second axial position where a first distal portion of the valve and at least part of the distal shoulder are within the jaws, and where a first proximal portion of the valve and the proximal shoulder are outside of the jaws proximal to the proximal end of the jaws; closing and opening the jaws with the valve and delivery device in the second axial position; repositioning the valve and delivery device from the second axial position to a third axial position where a second distal portion of the valve and at least part of the distal shoulder are within the jaws, and where a second proximal portion of the valve and the proximal shoulder are outside of the jaws proximal to the proximal end of the jaws, wherein the second distal portion is axially shorter than the first distal portion, and the second proximal portion is axially longer than the first proximal portion; closing and opening the jaws with the valve and delivery device in the third axial position; repositioning the valve and delivery device from the third axial position to a fourth axial position where the entire valve and at least part of the proximal shoulder of the delivery device are within the jaws, and where the entire distal shoulder of the delivery device is outside of the jaws distal to the distal end of the jaws; and closing and opening the jaws with the valve and delivery device in the fourth position.

Example 2. The method of any example herein, particularly example 1, wherein the first distal portion of the valve includes an outer skirt of the valve.

Example 3. The method of any example herein, particularly any one of examples 1-2, wherein the first distal portion of the valve comprises approximately one half of an axial length of the valve.

Example 4. The method of any example herein, particularly any one of examples 1-3, wherein the second distal portion of the valve includes a distal portion of the outer skirt.

Example 5. The method of any example herein, particularly any one of examples 1-4, wherein the second distal portion of the valve comprises approximately one fourth of an axial length of the valve.

Example 6. The method of any example herein, particularly any one of examples 1-5, wherein the valve is oriented around the delivery device with a blood inflow end of the valve adjacent the distal shoulder and a blood outflow end of the valve adjacent a proximal shoulder.

Example 7. The method of any example herein, particularly any one of examples 1-6, wherein closing and opening the jaws with the valve and delivery device in the first axial position comprises radially compressing and releasing the distal shoulder.

Example 8. The method of any example herein, particularly any one of examples 1-7, wherein closing and opening the jaws with the valve and delivery device in the second axial position comprises radially compressing and releasing the distal shoulder.

Example 9. The method of any example herein, particularly any one of examples 1-8, wherein closing and opening the jaws with the valve and delivery device in the third axial position comprises radially compressing and releasing the distal shoulder.

Example 10. The method of any example herein, particularly any one of examples 1-9, wherein closing and opening the jaws with the valve and delivery device in the fourth axial position comprises radially compressing and releasing the proximal shoulder.

Example 11. The method of any example herein, particularly any one of examples 1-10, wherein closing the jaws with the valve and delivery device in the fourth axial position compresses a proximal portion of the balloon and causes fluid in the balloon to travel distally into a distal portion of the balloon that is outside of the jaws distal to the distal end of the jaws.

Example 12. The method of example 11, wherein fluid travelling distally into the distal portion of the balloon causes the distal portion of the balloon to partially inflate and expand radially.

Example 13. The method of example 12, wherein the distal portion of the balloon expands radially to a diameter that is greater than a crimped diameter of the distal end of the valve.

Example 14. The method of any example herein, particularly any one of examples 1-13, further comprising, after closing and opening the jaws with the valve and delivery device in the fourth position, removing the delivery device and valve from the crimping device with the valve crimped over the balloon between the proximal and distal shoulders, and inserting the delivery device and valve into a patient.

Example 15. A method of crimping a prosthetic heart valve onto a delivery device, comprising: inserting the valve into a crimping device in a radially expanded state such that the valve is positioned within crimping jaws of the crimping device, the crimping jaws having a proximal end and a distal end; positioning an inflatable balloon of the delivery device within the valve, the delivery device comprising a proximal shoulder and a distal shoulder positioned within the balloon; positioning the valve and the delivery device in a first axial position where a first distal portion of the valve and at least part of the distal shoulder are within the jaws between the proximal and distal ends of the jaws, and where a first proximal portion of the valve and the proximal shoulder are outside of the jaws proximal to the proximal end of the jaws; closing and opening the jaws with the valve and delivery device in the first axial position, such that the valve is partially crimped onto the balloon between the proximal shoulder and the distal shoulder; repositioning the valve and delivery device from the first axial position to a second axial position where a second distal portion of the valve and at least part of the distal shoulder are within the jaws, and where a second proximal portion of the valve and the proximal shoulder are outside of the jaws proximal to the proximal end of the jaws, wherein the second distal portion is axially shorter than the first distal portion, and the second proximal portion is axially longer than the first proximal portion; closing and opening the jaws with the valve and delivery device in the second axial position; repositioning the valve and delivery device from the second axial position to a third axial position where a majority of the valve and at least part of the proximal shoulder of the delivery device are within the jaws, and where the distal shoulder of the delivery device is outside of the jaws distal to the distal end of the jaws; and closing and opening the jaws with the valve and delivery device in the third position; wherein closing the jaws with the valve and delivery device in the third axial position compresses a proximal portion of the balloon and causes fluid in the balloon to travel distally into a distal portion of the balloon that is outside of the jaws distal to the distal end of the jaws, wherein fluid travelling distally into the distal portion of the balloon causes the distal portion of the balloon to inflate and expand radially.

Example 16. The method of any example herein, particularly example 15, wherein fluid travelling distally into the distal portion of the balloon causes the distal portion of the balloon to expand radially to a diameter that is greater than a crimped diameter of a distal end of the valve.

Example 17. The method of any example herein, particularly any one of examples 15-16, wherein the first distal portion of the valve includes an outer skirt of the valve.

Example 18. The method of any example herein, particularly any one of examples 15-17, wherein the first distal portion of the valve comprises approximately one half of an axial length of the valve.

Example 19. The method of any example herein, particularly any one of examples 15-18, wherein the second distal portion of the valve includes a distal portion of the outer skirt.

Example 20. The method of any example herein, particularly any one of examples 15-19, wherein the second distal portion of the valve comprises approximately one fourth of an axial length of the valve.

Example 21. The method of any example herein, particularly any one of examples 15-20, wherein the valve is oriented around the delivery device with a blood inflow end of the valve adjacent the distal shoulder and a blood outflow end of the valve adjacent a proximal shoulder.

Example 22. The method of any example herein, particularly any one of examples 15-21, wherein closing and opening the jaws with the valve and delivery device in the first axial position comprises radially compressing and releasing the distal shoulder.

Example 23. The method of any example herein, particularly any one of examples 15-22, wherein closing and opening the jaws with the valve and delivery device in the second axial position comprises radially compressing and releasing the distal shoulder.

Example 24. The method of any example herein, particularly any one of examples 15-23, wherein closing and opening the jaws with the valve and delivery device in the third axial position comprises radially compressing and releasing the proximal shoulder.

Example 25. A device for crimping prosthetic heart valves, comprising: first jaws having an open position and a fully closed position, wherein the first jaws have a first inner diameter in the fully closed position; and second jaws having an open position and a fully closed position, wherein the second jaws have a second inner diameter in the fully closed position; wherein the second inner diameter is smaller than the first inner diameter.

Example 26. The device of any example herein, particularly example 25, wherein the first jaws and the second jaws are axially side-by-side.

Example 27. The device of any example herein, particularly any one of examples 25-26, wherein the first jaws and the second jaws are in contact with each other.

Example 28. The device of any example herein, particularly any one of examples 25-27, wherein the first jaws have a greater axial dimension than the second jaws.

Example 29. The device of any example herein, particularly any one of examples 25-28, wherein the first inner diameter and the second inner diameter are selected to correspond to desired outer diameters of prosthetic heart valve that is crimped by the device.

Example 30. The device of any example herein, particularly any one of examples 25-29, wherein the first jaws and the second jaws are actuated at the same time using a common actuator.

Example 31. The device of any example herein, particularly any one of examples 25-30, wherein the device is configured to crimp a valve with a blood outflow end of the valve in contact with the first jaws and a blood inflow end of the valve in contact with the second jaws, such that the blood inflow end of the valve is compressed to a smaller outer diameter than the blood outflow end of the valve.

Example 32. The device of any example herein, particularly any one of examples 25-31, wherein the device is configured to crimp a valve with a blood inflow end of the valve in contact with the first jaws and a blood outflow end of the valve in contact with the second jaws, such that the blood outflow end of the valve is compressed to a smaller outer diameter than the blood inflow end of the valve.

Example 33. The device of any example herein, particularly any one of examples 25-32, wherein the first jaws are at least two times as wide as the second jaws along an axial dimension.

Example 34. The device of any example herein, particularly any one of examples 25-33, wherein the first jaws are at least five times as wide as the second jaws along an axial dimension.

Example 35. The device of any example herein, particularly any one of examples 25-34, wherein the inner diameter of the first jaws is at least twice as large as the inner diameter of the second jaws.

Example 36. The device of any example herein, particularly any one of examples 25-35, wherein the second jaws in the fully closed position comprise a tapered inner surface that varies in inner diameter along at least part of its axial length.

Example 37. The device of any example herein, particularly any one of examples 25-36, wherein the first and second jaws in their open positions have equal inner diameters.

The invention claimed is:

1. A method of crimping a prosthetic heart valve onto a delivery device, comprising:
   inserting the valve into a crimping device in a radially expanded state such that the valve is positioned within crimping jaws of the crimping device, the crimping jaws having a proximal end and a distal end;
   positioning an inflatable balloon of the delivery device within the valve, the delivery device comprising a proximal shoulder and a distal shoulder positioned within the balloon;
   positioning the valve and the delivery device in a first axial position where the valve and at least part of the distal shoulder are within the jaws between the proximal and distal ends of the jaws, and where the entire proximal shoulder of the delivery device is outside of the jaws proximal to the proximal end of the jaws;
   closing and opening the jaws with the valve and delivery device in the first axial position, such that the valve is at least partially crimped onto the balloon between the proximal shoulder and the distal shoulder;
   repositioning the valve and delivery device from the first axial position to a second axial position where a first distal portion of the valve and at least part of the distal shoulder are within the jaws, and where a first proximal portion of the valve and the proximal shoulder are outside of the jaws proximal to the proximal end of the jaws;
   closing and opening the jaws with the valve and delivery device in the second axial position;
   repositioning the valve and delivery device from the second axial position to a third axial position where a second distal portion of the valve and at least part of the distal shoulder are within the jaws, and where a second proximal portion of the valve and the proximal shoulder are outside of the jaws proximal to the proximal end of the jaws, wherein the second distal portion is axially shorter than the first distal portion, and the second proximal portion is axially longer than the first proximal portion;
   closing and opening the jaws with the valve and delivery device in the third axial position;
   repositioning the valve and delivery device from the third axial position to a fourth axial position where the entire valve and at least part of the proximal shoulder of the delivery device are within the jaws, and where the entire distal shoulder of the delivery device is outside of the jaws distal to the distal end of the jaws; and
   closing and opening the jaws with the valve and delivery device in the fourth position.

2. The method of claim 1, wherein the first distal portion of the valve includes an outer skirt of the valve.

3. The method of claim 1, wherein the second distal portion of the valve includes a distal portion of an outer skirt.

4. The method of claim 1, wherein the valve is oriented around the delivery device with a blood inflow end of the valve adjacent the distal shoulder and a blood outflow end of the valve adjacent the proximal shoulder.

5. The method of claim 1, wherein closing and opening the jaws with the valve and delivery device in the first axial position comprises radially compressing and releasing the distal shoulder.

6. The method of claim 1, wherein closing and opening the jaws with the valve and delivery device in the second axial position comprises radially compressing and releasing the distal shoulder.

7. The method of claim 1, wherein closing and opening the jaws with the valve and delivery device in the third axial position comprises radially compressing and releasing the distal shoulder.

8. The method of claim 1, wherein closing and opening the jaws with the valve and delivery device in the fourth axial position comprises radially compressing and releasing the proximal shoulder.

9. The method of claim 1, wherein closing the jaws with the valve and delivery device in the fourth axial position compresses a proximal portion of the balloon and causes fluid in the balloon to travel distally into a distal portion of the balloon that is outside of the jaws distal to the distal end of the jaws;
   wherein fluid travelling distally into the distal portion of the balloon causes the distal portion of the balloon to partially inflate and expand radially; and
   wherein the distal portion of the balloon expands radially to a diameter that is greater than a crimped diameter of a distal end of the valve.

10. A method of crimping a prosthetic heart valve onto a delivery device, comprising:
   inserting the valve into a crimping device in a radially expanded state such that the valve is positioned within crimping jaws of the crimping device, the crimping jaws having a proximal end and a distal end;
   positioning an inflatable balloon of the delivery device within the valve, the delivery device comprising a proximal shoulder and a distal shoulder positioned within the balloon;
   positioning the valve and the delivery device in a first axial position where a first distal portion of the valve and at least part of the distal shoulder are within the jaws between the proximal and distal ends of the jaws, and where a first proximal portion of the valve and the proximal shoulder are outside of the jaws proximal to the proximal end of the jaws;
   closing and opening the jaws with the valve and delivery device in the first axial position, such that the valve is partially crimped onto the balloon between the proximal shoulder and the distal shoulder;
   repositioning the valve and delivery device from the first axial position to a second axial position where a second distal portion of the valve and at least part of the distal shoulder are within the jaws, and where a second proximal portion of the valve and the proximal shoulder are outside of the jaws proximal to the proximal end of the jaws, wherein the second distal portion is axially shorter than the first distal portion, and the second proximal portion is axially longer than the first proximal portion;
   closing and opening the jaws with the valve and delivery device in the second axial position;
   repositioning the valve and delivery device from the second axial position to a third axial position where a majority of the valve and at least part of the proximal shoulder of the delivery device are within the jaws, and where the distal shoulder of the delivery device is outside of the jaws distal to the distal end of the jaws; and
   closing and opening the jaws with the valve and delivery device in the third position;

wherein closing the jaws with the valve and delivery device in the third axial position compresses a proximal portion of the balloon and causes fluid in the balloon to travel distally into a distal portion of the balloon that is outside of the jaws distal to the distal end of the jaws, wherein fluid travelling distally into the distal portion of the balloon causes the distal portion of the balloon to inflate and expand radially.

11. The method of claim 10, wherein fluid travelling distally into the distal portion of the balloon causes the distal portion of the balloon to expand radially to a diameter that is greater than a crimped diameter of a distal end of the valve.

12. The method of claim 10, wherein the first distal portion of the valve includes an outer skirt of the valve.

13. The method of claim 10, wherein the second distal portion of the valve includes a distal portion of an outer skirt.

14. The method of claim 10, wherein the valve is oriented around the delivery device with a blood inflow end of the valve adjacent the distal shoulder and a blood outflow end of the valve adjacent the proximal shoulder.

15. The method of claim 10, wherein closing and opening the jaws with the valve and delivery device in the first axial position comprises radially compressing and releasing the distal shoulder.

16. The method of claim 10, wherein closing and opening the jaws with the valve and delivery device in the second axial position comprises radially compressing and releasing the distal shoulder.

17. The method of claim 10, wherein closing and opening the jaws with the valve and delivery device in the third axial position comprises radially compressing and releasing the proximal shoulder.

* * * * *